United States Patent [19]

LaCourse

[11] 4,243,027
[45] Jan. 6, 1981

[54] HIP STABILIZER

[76] Inventor: Y. Ronald LaCourse, 25 Cheyenne Crescent, Whitesboro, N.Y. 13492

[21] Appl. No.: 953,076

[22] Filed: Oct. 20, 1978

[51] Int. Cl.³ .............................................. A61F 5/01
[52] U.S. Cl. .................. 128/80 F; 308/3.9; 308/6 R
[58] Field of Search .................. 128/80 F, 80 R, 83.5, 128/80 A, 80 B, 88, 87 R, 84 H, 84 R, 85; 403/116, 117, 61, 80, 82, 119; 308/3.9, 6 R; 33/149 R, 149 H; 49/346

[56] References Cited

U.S. PATENT DOCUMENTS

| 2,207,466 | 7/1940 | Martens et al. | 308/6 R |
|---|---|---|---|
| 2,578,108 | 12/1951 | Thornton | 403/116 |
| 2,632,439 | 3/1953 | Hickerson | 128/80 F |
| 2,676,042 | 4/1954 | Roethel | 49/346 |
| 2,690,176 | 9/1954 | Nelson | 128/80 F |
| 2,705,491 | 4/1955 | Hickerson | 128/80 F |
| 2,772,901 | 12/1956 | Roethel | 403/61 |
| 3,552,786 | 5/1969 | Schmid | 403/116 |
| 3,667,161 | 6/1972 | Sassano | 49/346 |
| 3,697,031 | 10/1972 | Glickman et al. | 403/61 |
| 3,902,482 | 9/1975 | Taylor | 403/116 |
| 4,030,378 | 6/1977 | Kroesser | 403/116 |

Primary Examiner—Robert W. Michell
Assistant Examiner—Arthur S. Rose
Attorney, Agent, or Firm—Bruns & Jenney

[57] ABSTRACT

An orthopedic device for precisely controlling the leg and hip movement of a handicapped individual in order to stabilize the position of the hips when walking and thus promote normal back muscle development and body growth. The apparatus of the invention includes a guide member and a slide mechanism operatively associated therewith. The guide member is rigidly connected to one of a pair of leg braces while the slide mechanism is similarly connected to the other leg brace of the pair. A very precise motion is translated from the guide and slide mechanism to the leg braces which directs the legs of the individual through a path of travel that holds the hips and pelvic region in a relatively normal horizontally aligned position.

12 Claims, 4 Drawing Figures

HIP STABILIZER

BACKGROUND OF THE INVENTION

This invention relates to apparatus for use in the field of orthopedics and, in particular, to means for precisely controlling the movement of a handicapped individual's legs in order to stabilize the hips and thus promote normal muscle development and body growth.

The most pertinent prior art known to the applicant at the time of filing this application is contained in the following U.S. Pat. Nos.: 2,632,439; 2,690,176 and 2,705,491.

The prior art devices described in the above-noted patents all involve apparatus for use in conjunction with leg braces which are specifically designed to prevent the legs of the wearer from scissoring or crossing over when the individual is walking. Although all these devices provide a certain amount of lateral stability to the legs, they can not deliver the precise leg movement that is needed to hold the hips of the user in a relatively normal horizontally aligned position when the individual is walking. Many crippling diseases and/or bodily defects make it extremely difficult for the afflicted person to walk even when aided by leg braces. Usually a great deal of strenuous body movement must be used in order to propel the legs forward. As a consequence, the hips and the pelvic region are abnormally forced out of position leading to a weakening of the back muscles and in certain cases, improper body development. All of the prior art devices fail to deliver the precision needed to hold the hips and pelvis of the handicapped individual in proper alignment as the legs swing through a normal walking gait.

SUMMARY OF THE INVENTION

It is therefore an object of the present invention to improve orthopedic devices for aiding handicapped people in walking.

Another object of the present invention is to strengthen the back muscles and promote body growth of a person that is afflicted with a crippling condition.

Yet another object of the present invention is to provide a walking aid for a handicapped individual which will accurately control the movements of the legs whereby the legs move through a prescribed path of travel which serves to hold the pelvic region and hips of the user in a normal horizontal position.

A further object of the present invention is to stabilize the hip movement of a crippled individual who is required to wear leg braces in order to walk.

These and other objects of the present invention are attained by means of apparatus that is adapted to be affixed to a pair of leg braces and which includes a guide member having a contoured control surface internally formed therein, a slide mechanism operatively associated with the guide member having a follower arranged to move back and forth over the control surface formed in the guide, a first mounting bracket for affixing the guide to one leg brace, and a second mounting bracket for affixing the slide mechanism to the other leg brace whereby a predetermined motion is translated from the control surface to the braces.

A BRIEF DESCRIPTION OF THE DRAWINGS

For a better understanding of these and other objects of the present invention, the following detailed description of the invention is to be read in connection with the accompanying drawings wherein.

DESCRIPTION OF THE INVENTION

Figure 1:
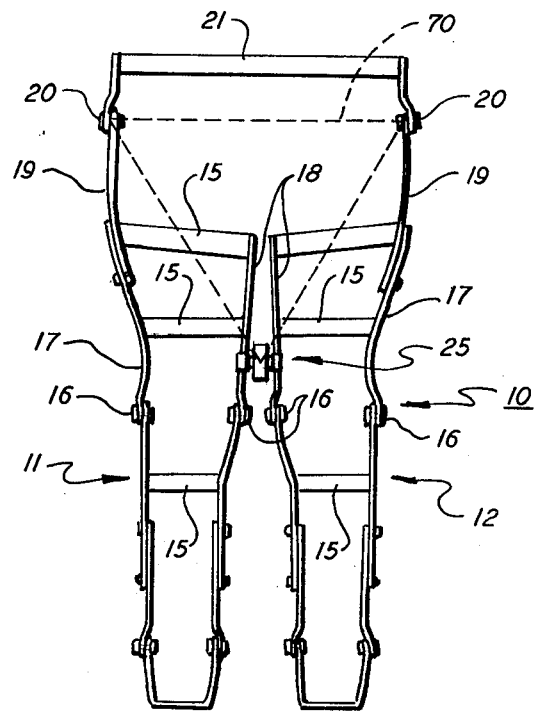
FIG. 1 is a front elevation showing a pair of leg braces that are operatively connected to a hip stabilizer embodying the teachings of the present invention.

Referring initially to FIG. 1, there is illustrated a pair of leg braces, generally referenced 10, that are of rather conventional design. As is typical in the art, both the right leg brace 11 and the left leg brace 12 are symetrical. Each brace is made up of a series of vertical metal bands or straps that are strategically linked together at vital points by means of pivots to permit the brace to flex. The vertical bands, in turn, are interconnected by arcuate shaped, horizontally aligned, members that are generally noted as 15. A relatively strong, self-standing unit is thus provided which is capable of aiding the wearer in standing and, to some degree, in walking.

Each brace further includes a vertically aligned outer thigh band 17 and similarly aligned inner thigh band 18. Both the outer and inner thigh bands are movably connected to the leg brace at the knee joints by means of pivots 16—16. A contoured body band 19 is also attached to the outer thigh piece of each brace and is connected by a hip pivot 20 to a body strap 21. The body strap encircles the waist of the user and thus provides some further body support.

As noted above, most leg braces are designed primarily to help a weakened or handicapped person to stand and, to some extent, to walk. Many such individuals, because of the nature of their afflictions, need further help in walking. Even when equipped with braces, it has been found that the legs can only be moved with the expenditure of a great deal of energy and severely contorted hip movements which lead to a weakening of the back muscles and other associated defects.

A hip stabilizer which embodies the teachings of the present invention and which overcomes many of the difficulties found in the prior art is shown at 25 in FIG. 1. The stabilizer is secured to the two inner thigh bands of each brace at a point above the knee joint pivot. In assembly, the stabilizer is located at the midspan point between the braces when the legs of the wearer are situated in a normal walking or standing position. As will be explained in greater detail below, the unit operates to direct the legs of the user through a very exact path of travel which closely simulates a normal walking gait. Because the braces, and thus the legs of the wearer, are not permitted to deviate from this prescribed path of motion, the hips of the individual, which form a part of the total system, are held in a normal, generally horizontal position.

Figure 2:
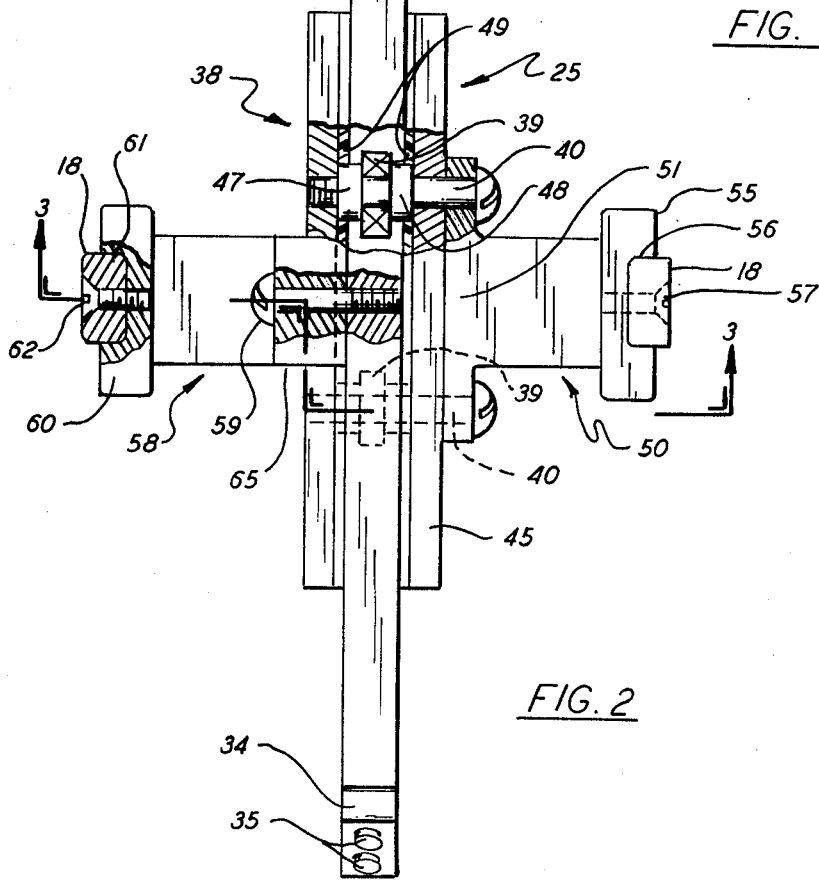
FIG. 2 is an enlarged top view of the hip stabilizer shown in FIG. 1 with portions broken away to more clearly illustrate the interaction of the various components thereof.
Figure 3:
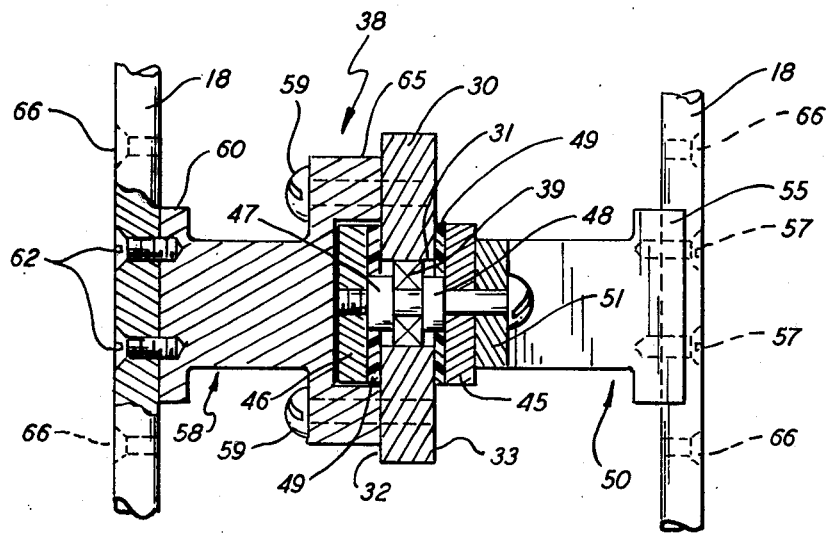
FIG. 3 is a section taken along lines 3—3 in FIG. 2 which further illustrate the component parts of the hip stabilizer of the present invention.
Figure 4:
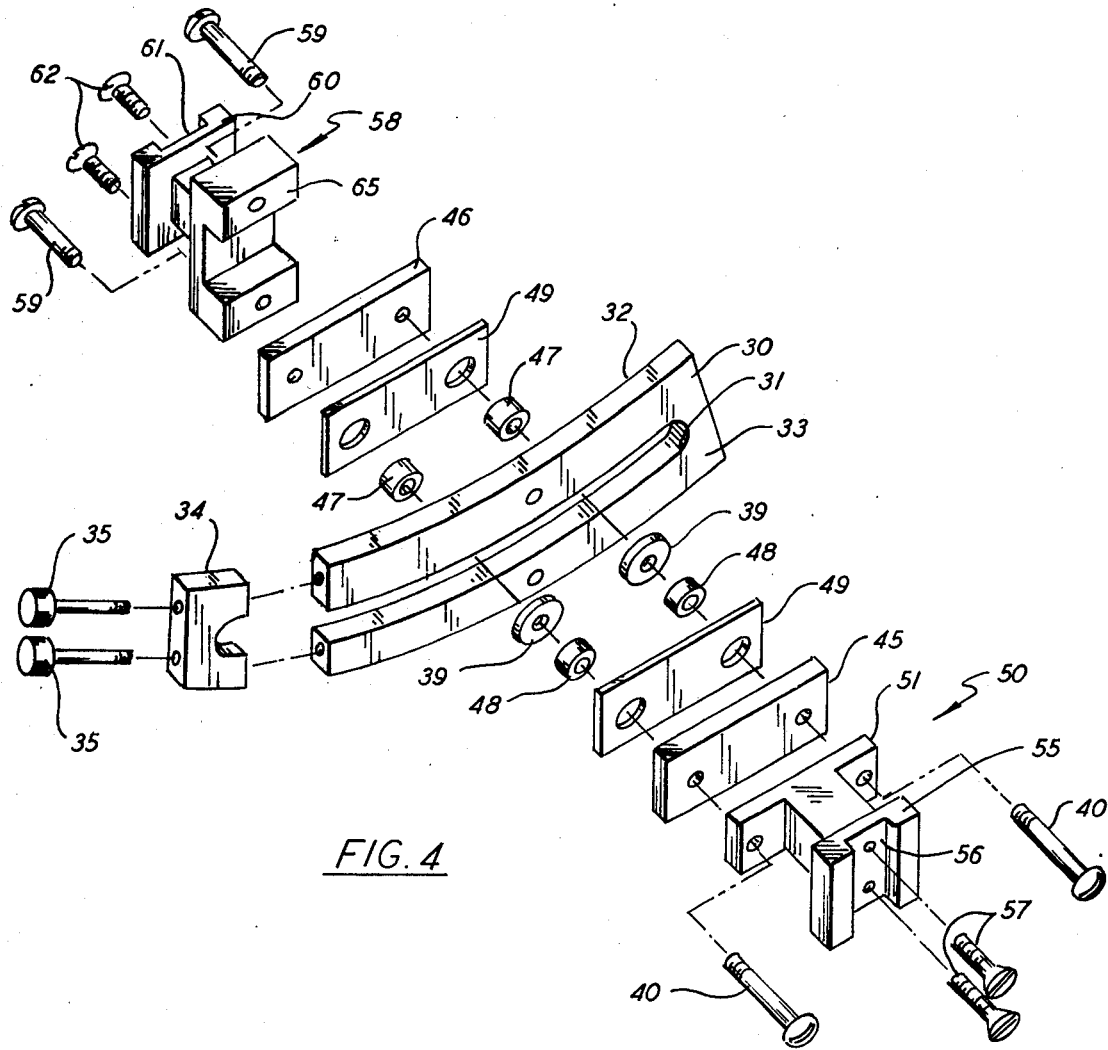
FIG. 4 is an exploded view in perspective showing the component parts of the stabilizer in greater detail.

Referring now with further reference to FIGS. 2-4, the hip stabilizer of the present invention includes a central guide member 30 that is of generally rectangular form and which contains a contoured slotted hole 31 therein. The contoured hole passes through the two side walls 32, 33 of the guide member and is generally arcuate in shape. An end cap 34 is fitted upon one end of the guide member and is held in position by means of a pair of thumb screws 35—35. The end cap encloses the contoured hole and provides clear and easy access thereto when the cap is removed from the guide member.

A slide mechanism 38 is adapted to ride back and forth in sliding contact against the side walls of the guide member. A pair of ball bearings or roller bearings 39—39 are carried in the slide and are adapted to be centrally located within the contoured hole formed in the guide. Each bearing is sized to provide a close running fit between the outer periphery thereof and the inner walls of the hole so that the bearings can roll back and forth within the hole with little or no wall clearance. The bearings are rotatably supported upon shafts 40—40 that are headed at one end and threaded at the outer. In assembly, the shafts are passed through a face block 45 and threaded into a second backing block 46 to secure the two blocks against the opposing side walls of the guide member.

Cylindrical spacers 47, 48 are also mounted upon each shaft on either side of the roller bearing. The spacers are adapted to act between the side walls of the blocks and the bearing to hold the bearing centered in the contoured hole of the guide member when the blocks are brought into contact with the side walls of the guide member.

A pair of thin shims 49—49 are interposed between the side walls of the guide member and the block positioned adjacent thereto. The shims are fabricated of a low friction material, such as Teflon or the like, which allows the blocks to slide easily over the side wall surfaces of the guide member. It should be clear to one skilled in the art that, alternatively, the blocks can be similarly formed or surface coated of the low friction material without departing from the teachings of the present invention.

A left hand mounting bracket 50 is rigidly secured to the slide mechanism by passing the headed end of the two shafts through mounting flange 51. The bracket, in assembly, is drawn securely against the face block of the slide mechanism as the two shafts are threaded into the backing block. The bracket also includes an outer recessed flange 55 that has a cut out 56 formed in its face and in which the inner thigh band 18 of one of the braces is snuggly seated. The band is secured to the bracket via a pair of flat head screws 57—57 which pass through the bracket and are threadably received within the body of the bracket.

A second right hand mounting bracket 58 is rigidly secured to the side wall 32 of the guide member by means of screws 59. The second mounting bracket also includes an outer recessed flange 60 adapted to receive the inner thigh band of the other leg brace within recess 61. Again the band is locked to the bracket using flat headed screws 62—62. The proximal end of bracket 58, which is secured to the side wall of the guide member, is machined or otherwise formed to establish a depending channel section 65. The web of the channel spans the backing block of the slide mechanism. Sufficient clearance is provided between the inside surfaces of the channel section and the outside surfaces of the backing block to enable the block to reciprocate freely within the channel.

As best seen in FIG. 3 each of the inner thigh bands is provided with a series of equally spaced holes 66 for receiving the above-noted flat headed bracket mounting screws therein. The holes extend upwardly from the knee joint pivots and allow the brackets to be selectively positioned along the length of the bands. This, in turn, enables the stabilizer mechanism to be adjustably located in assembly.

Referring once again to FIG. 1, the theory of operation of the stabilizer will be explained in greater detail with reference to the triangle 70 shown in dotted lines. With the stabilizer rigidly secured to the braces as described above, the stabilizer and the hips of the wearer describe the corners of an inverted equilateral triangle as shown with the stabilizer lying at the apex of the triangle and the hips being located at the other two corners. As can be seen, the pelvis of the wearer is thus aligned along the base of the triangle between the hips. In practice, the contoured slotted hole formed in the guide member is cut in the shape of an arc or chord of a circle. In assembly, the guide is located so that the center of the arc lies generally upon the base of the triangle.

The two sliding blocks of the slide mechanism are clamped against the opposed side walls of the guide member via the threaded shafts with sufficient force to prevent the mechanism from twisting or moving laterally in assembly. The blocks, acting through the shims, are allowed to slide freely over the guide walls in close contact therewith. As a result of this arrangement, a very precise motion is translated to the slide through the roller bearings as they move in contact over the walls of the contoured hole. As can be seen with reference to FIG. 1, this motion is confined within a vertical plane passing through the apex of the triangle. As should now be evident, by this construction, the length of the triangle legs, as well as the angular relationship therebetween, can not appreciably change as the leg braces are moved back and forth over the prescribed path of travel. Accordingly, the hips of the wearer, and the pelvic region therebetween, is securely held in a normal horizontal plane as depicted by the base line of the triangle when the legs of the wearer are moved at a walking gait. This, in turn, allows the back of the wearer, and in particular the back muscles, to develop normally thus preventing slouching and the like.

It should be further noted that it is extremely difficult to put on the braces when they are secured together as by the present stabilizer. This difficulty is herein overcome by simply removing the end cap of the guide member and separating the two braces. Once the braces are properly secured to the legs the slide can be easily inserted into the guide and the end cap once again secured to the end of the guide member.

While this invention has been described with reference to the disclosure above, it is not necessarily confined to the detail as set forth but is intended to cover any modifications within the scope of the following claims.

I claim:

1. Apparatus for stabilizing the hips of a crippled individual including a pair of leg braces, one brace for the left leg of a person and another for the right leg of a person, wherein the improvement comprises
    a guide member having two opposed vertical side walls and a contoured slotted hole passing through said vertical side walls, the slotted hole being contoured to describe a predetermined path of travel within a generally vertical plane,
    a slide mechanism having two opposed plates that are arranged to ride in close sliding contact with the vertical side walls of the guide and having a follower that is seated within the contoured slotted hole of the guide which provides a close running fit therewith to allow the slide mechanism to move back and forth along the path of travel as described by said slotted hole, a first mounting bracket secured at one end of said guide member and at the other end to one of said pair of leg braces, and a second mounting bracket secured at one end to said slide mechanism and at the other end to the other one of said pair of leg braces whereby the motion of the braces is limited to that described by the contoured slotted hole.

2. Apparatus for stabilizing the hips of a crippled individual who is required to wear a pair of leg braces including a guide member having two opposed vertical side walls and a contoured slotted hole passing through said vertical side walls, the slotted hole being contoured to describe a predetermined path of travel within a generally vertical plane, a slide mechanism having two opposed plates that are arranged to ride to close sliding contact with the vertical side walls of the guide and having a follower that is seated within the contoured slotted hole of the guide which provides a close running fit therewith to allow the slide mechanism to move back and forth along said path of travel described by said slotted hole.

said follower further including a pair of spaced apart roller bearings that are rotatably mounted upon shafts passing laterally through the slotted hole, said shafts being secured in said plates, a first mounting bracket secured at one end to said guide member and at the other end to one of a pair of leg braces, and a second mounting bracket secured at one end to said slide mechanism and at the other end to the other of said pair of leg braces.

3. The apparatus of claim 2 which further includes a pair of spacers mounted upon each of the bearing shafts for centrally locating the bearings within the contoured slotted hole of the guide member.

4. The apparatus of claim 2 which further includes a low friction shim being positioned between the two opposed plates of the slide mechanism and the vertical side walls of the guide member.

5. The apparatus of claim 2 which further includes adjusting means operatively associated with both of the leg braces for vertically positioning the mounting brackets upon said braces.

6. The apparatus of claim 2 wherein said guide member further includes a removable end cap for enclosing the contoured slotted hole therein whereby the slide mechanism can be slidably moved into and out of said hole when the end cap is removed.

7. Apparatus for stabilizing the hips of a crippled individual who has difficulty in walking including a pair of leg braces wherein each brace includes a knee joint and a vertically aligned inner band extending upwardly from said knee joint, a guide member secured to the inner band of one of said pair of braces, the guide member having two opposed vertical side walls and an arcuate shaped hole passing through the side walls with the radius lying generally in a plane that is parallel with said side walls, a slide mechanism being securely affixed to the inner band of the other brace of said pair of braces, the slide mechanism having two opposed slide elements that are arranged to ride in close sliding contact against the vertical side walls of the guide member and a follower seated within the arcuate shaped hole passing through the guide member which has a close running fit with the top and bottom walls of said hole whereby the motion of the braces is limited to that described by the arcuate shaped opening.

8. The apparatus of claim 7 wherein the contact faces of the two slide elements are provided with a low friction material whereby the elements move freely in sliding contact along the side walls of the guide member.

9. Apparatus for stabilizing the hips of a crippled individual who has difficulty in walking including a pair of leg braces wherein each brace includes a knee joint and a vertically aligned inner band extending upwardly from said knee joint, a guide member secured to the inner band of one of said pair of braces, the guide member having two opposed vertical side walls and an arcuate shaped hole passing through the side walls with the radius of the arc being generally in a plane that is parallel with said side walls, a slide mechanism being securely affixed to the inner band of the other brace, the slide mechanism having two opposed slide elements that are arranged to ride in sliding contact against the side walls of the guide member and a follower seated within the arcuate shaped hole, said follower having a close running fit with the inner wall of said arcuate shaped hole whereby the motion of the braces is limited to that described by the arcuate shaped hole, and said vertical bands being provided with a series of equally spaced holes by which the slide mechanism and the guide member can be adjustably secured thereto at selected locations.

10. The apparatus of claim 9 wherein the follower consists of two spaced apart roller bearings, each of which is mounted upon a shaft passing through the hole and is supported at its end in the slide elements.

11. The apparatus of claim 10 wherein the slide elements are rectangular blocks.

12. The apparatus of claim 9 which further includes an end cap removably mounted upon the guide member for enclosing one end of the hole whereby the slide mechanism can be slidably moved into and out of said hole when the end cap is removed.

* * * * *

UNITED STATES PATENT AND TRADEMARK OFFICE
CERTIFICATE OF CORRECTION

PATENT NO. : 4,243,027
DATED : Jan. 6, 1981
INVENTOR(S) : Y. Ronald LaCourse

It is certified that error appears in the above-identified patent and that said Letters Patent are hereby corrected as shown below:

Claim 2, Col. 5, line 24, "to" should be -- in --.

Signed and Sealed this

Seventh Day of April 1981

[SEAL]

Attest:

RENE D. TEGTMEYER

Attesting Officer     Acting Commissioner of Patents and Trademarks